(12) United States Patent
Krozer et al.

(10) Patent No.: US 9,701,765 B2
(45) Date of Patent: Jul. 11, 2017

(54) CUSTOMIZED MOLECULARLY IMPRINTED POLYMER (MIP) UNITS

(75) Inventors: Anatol Krozer, Göteborg (SE);
Kristina Reimhult, Mölndal (SE);
Björn Löfving, Göteborg (SE); Björn Malm, Hägersten (SE); Lei Ye, Lund (SE); Keiichi Yoshimatsu, Lund (SE)

(73) Assignee: RISE ACREO AB, Kista (SE)

( * ) Notice: Subject to any disclaimer, the term of this patent is extended or adjusted under 35 U.S.C. 154(b) by 657 days.

(21) Appl. No.: 13/147,631

(22) PCT Filed: Feb. 10, 2010

(86) PCT No.: PCT/EP2010/051629
§ 371 (c)(1),
(2), (4) Date: Nov. 9, 2011

(87) PCT Pub. No.: WO2010/092071
PCT Pub. Date: Aug. 19, 2010

(65) Prior Publication Data
US 2012/0045838 A1    Feb. 23, 2012

Related U.S. Application Data

(60) Provisional application No. 61/152,827, filed on Feb. 16, 2009.

(30) Foreign Application Priority Data

Feb. 16, 2009    (SE) ........................ 0950083

(51) Int. Cl.
*G01N 21/00*    (2006.01)
*C08F 8/14*    (2006.01)
(Continued)

(52) U.S. Cl.
CPC ................. *C08F 8/14* (2013.01); *B01J 20/26* (2013.01); *B01J 20/268* (2013.01); *C08F 2/14* (2013.01);
(Continued)

(58) Field of Classification Search
CPC ..... B01D 15/3852; B01J 20/26; B01J 20/268; B01J 2220/54; C08F 2/14; C08F 2/44; C08F 8/14; C08F 220/06; Y10T 428/2982
(Continued)

(56) References Cited

U.S. PATENT DOCUMENTS 4,046,667 A * 9/1977 Goetz ........................... 204/645
2003/0153001 A1* 8/2003 Soane ................. C08B 37/0021
435/7.1
(Continued)

FOREIGN PATENT DOCUMENTS

WO    WO 02/068958 A1    9/2002

OTHER PUBLICATIONS

International Search Report (PCT/ISA/210) issued on Jun. 28, 2010, by European Patent Office as the International Searching Authority for International Application No. PCT/EP2010/051629.
(Continued)

*Primary Examiner* — Rebecca M Fritchman
(74) *Attorney, Agent, or Firm* — Buchanan Ingersoll & Rooney P.C.

(57)    ABSTRACT

A method of manufacturing at least one customized MIP unit including: (a) providing at least one MIP unit having a surface including at least one target binding site configured to resemble a target molecule and surface-bound chargeable groups; (b) contacting the MIP unit(s) from the step (a) with at least one template molecule in a first solvent allowing the template molecule(s) to bind to the MIP unit(s); (c) passivating the surface-bound chargeable groups on the MIP
(Continued)

unit(s) by adding a passivating agent; and (d) removing the template molecule(s) by washing in a second solvent, wherein the passivating agent binds to the surface of the unit(s) through bonds which remain stable upon washing in the second solvent.

12 Claims, 5 Drawing Sheets

(51) Int. Cl.
  B01J 20/26     (2006.01)
  C08F 2/14      (2006.01)
  C08F 2/44      (2006.01)
  C08F 8/10      (2006.01)
  C08F 220/06    (2006.01)
  C08F 26/06     (2006.01)
  B01D 15/38     (2006.01)
  C08F 222/10    (2006.01)

(52) U.S. Cl.
  CPC .................. *C08F 2/44* (2013.01); *C08F 8/10* (2013.01); *C08F 220/06* (2013.01); *B01D 15/3852* (2013.01); *B01J 2220/54* (2013.01); *C08F 2222/1026* (2013.01); *G01N 2600/00* (2013.01); *Y10T 428/2982* (2015.01)

(58) Field of Classification Search
  USPC ........... 428/220, 402; 977/773, 774; 436/34, 436/164; 525/327.1, 330.1, 359.3
  See application file for complete search history.

(56) References Cited

U.S. PATENT DOCUMENTS

2009/0325147 A1* 12/2009 Jones, Jr. .......................... 435/5
2010/0261212 A1* 10/2010 Soman et al. .................. 435/21

OTHER PUBLICATIONS

R.J. Umpleby II et al., "Recognition Directed Site-Selective Chemical Modification of Molecularly Imprinted Polymers", Macromolecules, Nov. 20, 2001, pp. 8446-8452, vol. 34, No. 24.
K.D. Shimizu et al., "Selective Chemical Modification of Molecularly Imprinted Polymers", Polymeric Materials: Science & Engineering, 1984, pp. 847-848, vol. 84.
S. McNiven et al., "Enhancing the Selectivity of Molecularly Imprinted Polymers", Chemistry Letters, Jan. 1, 1997, pp. 1297-1298.
B. Sellergren, "Ionization State Selective Modification of Carboxyl Groups in Molecularly Imprinted Polymers: Supporting Evidence for a Binding Site Model", Macromolecules, Sep. 5, 2006, pp. 6306-6309, vol. 39, No. 18.

* cited by examiner

CUSTOMIZED MOLECULARLY IMPRINTED POLYMER (MIP) UNITS

TECHNICAL FIELD

The present invention relates to a molecularly imprinted polymer (MIP) unit having a surface comprising at least one target binding site, which is configured to resemble a target molecule, and to a method for the manufacture thereof.

The present invention also relates to the use of a MIP unit for the detection of a target molecule in a solution.

BACKGROUND OF THE INVENTION

Recently, the concern for monitoring water quality has increased world-wide. An area of particular concern is the release of health hazardous compounds, such as pharmaceuticals, pesticides, toxins etc. into the environment. Such compounds may persist in ground water and any other water that humans are exposed to.

The monitoring of hazardous compounds is crucial to ensure that the water people are exposed to is safe and free from contaminants that could cause health problems.

To date, several detection techniques exist, but monitoring water for chemical contaminants is difficult for a variety of reasons. For example, many compounds are present at very low concentrations making detection difficult. Furthermore, the detection sensitivity is often decreased by inhibitory compounds which may be present in environmental concentrates. As a result, many false positive signals are produced.

Currently, the research in the field of molecularly imprinted polymers, hereinafter referred to as MIPs, is accelerating. MIPs have attracted a lot of attention due to their ability to specifically recognize compounds such as drugs, hormones, proteins etc.

Molecular imprinting is a generic technology, which introduces recognition properties into synthetic polymers. MIPs are fabricated by synthesising highly cross-linked polymers from a mixture of functional monomers in the presence of an analyte, which functions as a template. After extraction of the analyte with a solvent, a molecular imprint is left in the polymer, which can recognise the same template molecule or its analogues.

MIPs are not as specific as antibodies, but possess high affinity towards specific targets (e.g., caffeine or sorbitol, see Feng, L. et. al. Biosensor for the determination of sorbitol based on molecularly imprinted electrosynthesized polymers. *Biosensors & Bioelectronics*, 2004, 19, 1513-1519) and usually have non-negligible affinity to similar molecules (e.g., MIPs prepared against Penicillin G display high affinity for not only the original template, but also other related β-lactam antibiotics, see Benito-Pena, E. et al. Molecular engineering of fluorescent penicillins for molecularly imprinted polymer assays. *Anal. Chem.*, 2006, 78, 2019-2027).

Depending on the application this may be a disadvantage, but it may be advantageous, too. For example, if one considers to apply the MIP-based sensing system to monitor environmental contaminants, e.g., pharmacological compounds in drinking water, one does not need to manufacture different MIPs for each contaminant, but only to each family of contaminants.

Current detection schemes, such as chromatography or electrophoresis paired with chemical sample treatment, and solid phase based extraction e.g. via MIP are time-consuming and unsuitable for use in or at the field. These techniques require the collection of a waste-water sample to be transported into a lab, where labor extensive extraction and analysis is required to detect the presence of a target compound of interest.

Furthermore, the MIP detection schemes currently available suffer from the generation of many false-positive signals, especially where MIPs have been produced by non-covalent imprinting.

Accordingly, there is a need in the art to provide an alternative approach for the detection of target molecules of interests, e.g. contaminants present in water and other environmental concentrates. Such a method should be convenient, inexpensive and prevent the generation of false-positive signals to a substantial degree. More specifically, such an approach should be capable of detection of target molecules in their actual contexts; i.e. in the environment where they are found; e.g. ground or waste water.

SUMMARY OF THE INVENTION

One object of the present invention is to fulfil the above mentioned need and to provide a MIP unit capable of specifically and selectively detecting target molecules of interest in their natural environment.

This and other objects of the present invention are achieved by a molecularly imprinted polymer (MIP) unit according to the appended claims.

Thus, in a first aspect the present invention relates to a molecularly imprinted polymer (MIP) unit having a surface comprising at least one target binding site and surface-bound chargeable groups. The target binding site is configured to resemble a target molecule of interest.

At least 80% of the total amount of surface-bound chargeable groups are located in the at least one target binding site enabling electrostatic interaction with a target molecule to occur in said site.

A MIP unit of the present invention comprises at least one target binding site which is configured to resemble a target molecule; i.e. the site is complementary to a target of interest in terms of its size and shape.

There are several factors affecting the interaction between a target and a MIP unit. First, the shape and the size of the target binding site should match that of a target molecule. Furthermore, hydrophobic interactions enhance the interaction with a target molecule in the target binding site. As target molecules are often charged entities, the presence of chargeable groups in the sites where the target molecules are to be bound allows for electrostatic interactions at such sites such that the target-polymer interaction is even further increased.

Accordingly, it is desirable to localize the surface charge; i.e. the presence of surface-bound chargeable groups, to the target binding sites while reducing the presence of chargeable groups at non-imprinted sites and other sites on the MIP unit surface.

During production of MIPs, especially through the non-covalent imprinting approach, many imprinted sites are typically formed. Some of these imprinted sites are "false" target binding sites, i.e. imprinted sites not complementary in size and shape to a target of interest. Due to the presence of surface-bound chargeable groups on such "false" sites and also on non-imprinted parts of the surface of the MIP unit, target molecules may still bind to the MIP units, resulting in a high rate of false positive signals. Such non-specific binding makes it difficult to determine whether the molecule adsorbed is indeed the one targeted.

The surface-bound chargeable groups typically result from the protonation or deprotonation of functional monomers used during imprinting.

In a MIP unit of the present invention, at least 80% of the total amount of surface-bound chargeable groups are located in the at least one target binding site enabling electrostatic interaction with a target molecule to occur in such site(s).

Typically, at least 90%, e.g. at least 95% of the total amount of surface-bound chargeable groups are located in such target binding sites.

Accordingly, target molecules are bound to the "correct" imprinted sites, i.e. target binding sites configured to resemble a target molecule and the generation of false positive signals is thereby reduced. Hence, MIP units according to the present invention are stable, robust and target specific.

A MIP unit according to the present invention may exist in the form of a particle having a diameter in the range of from 50 nm to 5 µm.

The size of the particle may be varied depending on the specific detection technique used.

Particles having a size less than 50 nm typically contain very few target binding sites and may be difficult to produce.

A MIP unit according to the present invention may also be in the form of a film having a thickness in the range of from 20 nm to 20 µm.

Such a film may be applied to (micro) electrodes in the form of e.g. interdigitated fingers. Upon target binding, a change in capacitance may be observed and detected.

A film in the above mentioned thickness range is suitable. When the thickness of the film is less than 20 nm, the film may be distorted by the polymer surface interaction, e.g. due to pinning of the polymer chains. In contrast, film thicknesses above 20 µm are impractical since the penetration of the target into the interior of the film is slower, and results in decreased occupation of target binding sites.

In alternative embodiments, the MIP unit further comprises an identity tag selected from the group comprising fluorophores, quantum dots and gold nanoparticles.

These embodiments are suitable for use if the detection takes place in turbid samples; i.e. samples comprising lots of other, non-imprinted background signal particles.

In another aspect, the present invention relates to the use of a MIP unit according to the above for the detection of a target molecule in a solution.

Accordingly, at least one MIP unit according to the above is contacted with a solution which may comprise a target molecule of interest.

The present inventors have found that this may be achieved by measuring the rate of agglomeration of the above described MIP units in a solution.

In a MIP unit according to the present invention, the effective charge state of the particle at a given pH will mainly be determined by the number of imprinted sites. This is due to the localization of surface-bound chargeable groups in the target binding sites, whereas the remaining particle surface (i.e. non-imprinted sites and non-specific imprinted sites) remains essentially uncharged.

Accordingly, upon binding with target molecules, the MIP units will have a net effective charge $Z_{eff}$ close to zero. This has an impact on the rate of agglomeration as the essentially uncharged MIP units will start to cluster.

The rate of agglomeration may thus be used as a measure of the amount of bound target molecules. The use of agglomeration to detect binding events with MIP units is unique per se' and is superior to other detection schemes in several aspects.

The agglomeration is directly related to the binding event. The MIP units will not agglomerate if the template compound is not bound.

As mentioned above, when detection takes place in turbid samples, several signal "disturbing" particles are present and these may interfere with the MIP units of the invention and give rise to undue clustering. In such situations, it is highly advantageous to use identity tags, e.g. fluorophores, quantum dots, gold nanoparticles to localize the specific binding events.

In alternative embodiments, the detection of a target molecule in a solution may be performed by measuring the net effective charge $Z_{eff}$ of the MIP units.

As mentioned hereinbefore, when target molecules bind to the MIP units of the invention, their net effective charge $Z_{eff}$ will change towards a $Z_{eff}$ close to zero. Accordingly, by simply measuring the $Z_{eff}$ it is possible to detect the presence of a target molecule of interest even without any agglomeration taking place.

A MIP unit of the invention may be used to specifically and selectively detect target molecules of interest at field; i.e. in the environment where they are typically found.

In yet another aspect, the present invention relates to a method of producing a customized MIP unit having the above mentioned characteristics.

The present inventors have found that one way to improve molecular imprints with respect to non-specific binding of a target in question is to effectively block non-specific imprinted sites formed during the MIP production. This is achieved by reducing the presence of surface-bound chargeable groups on such sites and on non-imprinted sites such that target molecules bind to "correct" target binding sites.

The method according to the invention comprises:

(a) providing at least one MIP unit having a surface comprising at least one target binding site configured to resemble a target molecule and surface-bound chargeable groups (b) contacting the MIP unit(s) from step (a) with at least one template molecule in a first solvent allowing the template molecule(s) to bind to the MIP unit(s)

(c) passivating the surface-bound chargeable groups on the MIP unit(s) by adding a passivating agent (d) removing the template molecule(s) by washing in a second solvent.

The passivating agent binds to the surface of the unit(s) through bonds which remain stable upon washing in the second solvent.

Accordingly, a MIP unit comprising chargeable groups mainly in the correct target binding site(s) is generated. The method of the invention is simple, inexpensive and allows for the mass production of customized MIP units having localized surface-bound chargeable groups within the target binding sites.

MIP units are contacted with template molecules in a first solvent. In embodiments, the first solvent has a pH which generates opposite polarities of the surface-bound chargeable groups and the template molecule(s), respectively, such that template molecules may bind to the units through electrostatic interactions. Accordingly, template molecules will bind to the MIP unit surface both specifically (i.e. in the target binding sites) and non-specifically. MIP units occupied by template molecules are thereby formed in step (b).

In order to remove non-specific binding at sites which are not configured to resemble a target of interest, as well as on non-imprinted sites on the MIP unit surface, the step of passivating, i.e. step (c) comprises removing template molecule(s) not specifically bound to the binding site(s) configured to resemble a target molecule such that surface-bound chargeable groups are exposed on said surface forming stable bonds between the passivating agent and the surface-bound chargeable groups.

The passivating agent will compete with the template molecules non-specifically bound to the surface such that these are removed in contact with the passivating agent. However, template molecules bound in the correct target binding sites will not be removed as these remain bound due to complementarity in size and shape, electrostatic interaction and hydrophobic interactions within these cavities.

Upon addition of a passivating agent, surface-bound chargeable groups become exposed on the surface of the MIP unit.

The passivating agent is capable of forming stable bonds with such exposed surface-bound chargeable groups and these bonds remain hydrolytically stable even after template elution by washing with a second solvent.

Such bonds may e.g. be selected from the group of ester bonds and amide bonds.

A MIP unit having a surface comprising at least one target binding site configured to resemble a target molecule is typically provided by polymerizing functional monomers in the presence of a template and a cross-linking agent.

In embodiments of the invention, step (a) and step (b) may be performed simultaneously by polymerizing functional monomers in the presence of the template molecule(s) in the first solvent. In such cases, the MIP units are formed when functional monomers polymerize in a first solvent and in the presence of template molecules.

In embodiments, the functional monomers are methacrylic functional monomers, e.g. methacrylic acid. Such monomers are suitable since their carboxyl group is a common hydrogen-bonding and acidic functional group in molecular imprinting.

If methacrylic monomers are used, the template compound may be selected from the group of beta-blockers, e.g. propranolol and betaxolol.

Suitable passivating agents used in combination with the above mentioned monomers and beta blockers are diazomethane, phenyldiazomethane and acyl halide.

These and other aspects of the invention will be apparent from and elucidated with reference to the embodiment(s) described hereinafter.

DETAILED DESCRIPTION OF THE INVENTION

Figure 1:
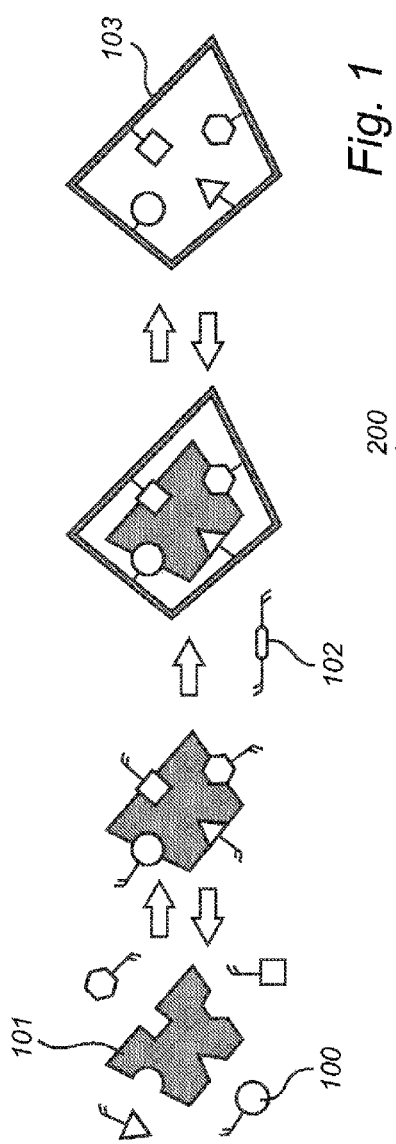
FIG. 1 illustrates the general procedure for molecular non-covalent imprinting

In FIG. 1, the general method steps of non-covalent imprinting are illustrated. Functional monomers 100 are mixed with at least one template molecule 101 which resembles at least one target molecule of interest.

A cross-linking agent 102 may be employed to control the morphology of the polymer matrix, stabilize the binding sites and provide mechanical stability. Suitable cross-linking agents depend on the monomers used for imprinting, and are known to a person skilled in the art.

The functional monomers 100 arrange themselves about the template molecule 101 based on non-covalent interactions such as hydrogen bonds, ionic bonds and hydrophobic interactions.

After polymerization, the template molecule 101 is eluted by washing in a solvent, and a molecular imprint 103 is left in the polymer, which is able to recognize the same template molecule 101 or its analogues. Accordingly, the resulting imprinted polymer possesses a permanent "memory" for the template molecules 103 enabling the MIP to bind target compounds closely related to the templates.

Empirically, it has been found that specificity increases with the number of bonds between the polymer and the binding "centra" on the target. This is illustrated by the different shapes on different sides of the template molecule 101.

The non-covalent imprinting approach is attractive as it is easy and applicable to a large number of templates. Furthermore, the templates can be easily removed from the polymer under mild conditions.

However, one drawback with non-covalent imprinting is the generation of imprinted sites which may act as "false" target binding sites and bind target molecules although not being complementary in size and shape. Such non-specific binding makes it difficult to determine whether the molecule adsorbed is indeed the one targeted. The generation of false positive signals (at least partly) depends on the presence of surface-bound chargeable groups on the MIP unit. Such surface-bound chargeable groups easily become charged in solution and electrostatically attract target compounds of opposite polarity.

Accordingly, it is desirable to localize surface-bound chargeable groups to the correct target binding sites on the MIP unit; i.e. the sites configured to resemble a target molecule of interest. This way, the MIP-target interaction is enhanced and the MIP unit becomes more selective.

As used herein, the term "chargeable group(s)" means a functional group which becomes a charged group when subjected to a solvent or a buffer which results in the deprotonation or protonation, respectively, of the functional group.

Examples of such chargeable functional groups are carboxyl groups and amino groups.

Figure 2:
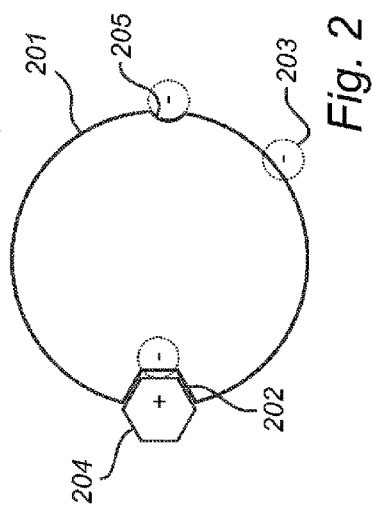
FIG. 2 illustrates a MIP unit according to the present invention.

A MIP particle 200 according to the present invention is illustrated in FIG. 2. The MIP particle 200 has a surface 201 comprising at least one target binding site 202 and surface-bound chargeable groups 203. In this case, the chargeable groups are negatively chargeable groups. The target binding site 202 is configured to resemble a target molecule 204.

As used herein, the term "configured to resemble a target molecule" means that the target binding site is essentially complementary in size and shape to a target molecule of interest. Accordingly, the target binding site may bind the same template molecule used in the imprinting process or target compounds which are closely related to the template used.

At least 80% of the total amount of surface-bound chargeable groups 203 are located in the at least one target binding site 202 enabling electrostatic interaction with a target molecule to occur in said site 202.

Typically during non-covalent imprinting, imprinted sites 205 which are not specific; i.e. not complementary in size and shape to a target of interest are formed. The presence of surface-bound chargeable groups 203 at such sites as well as on non-imprinted sites can result in false positive binding signals due to non-specific interaction with target molecules.

It is therefore desirable to concentrate the presence of surface-bound chargeable groups 203 to the target binding site(s) 202 which are configured to resemble a target of interest.

In a MIP particle according to the present invention, at least 80%, preferably at least 90%, e.g. at least 95% of the total amount of surface-bound chargeable groups 203 are located in the at least one target binding site 202. Accordingly, the interaction with a target molecule is enhanced, and is a result of both similarity in shape and size, electrostatic interaction and hydrophobic interactions in such sites 202.

The low presence of surface-chargeable groups 203 on the non-imprinted parts and the imprinted sites 205 which do not possess the selective properties of the target binding sites 202 will not be occupied by target molecules in a substantial degree. Accordingly, the detection sensitivity of the MIP particle 200 of the invention is improved and the production of false signals is reduced.

It should be noted that chargeable groups may also be present inside the particle; i.e. in pores in the polymeric network but these are typically not accessible to target molecules.

A MIP unit according to the present invention may be in the form of a particle or a film.

A MIP particle may be present in any shape, but is typically spherical with a diameter up to 10 μm, e.g. a diameter in the range of 50 nm to 5 μm, e.g. 50 nm to 1.5 μm.

The size of the particle may be varied depending on the specific detection technique used. If the detection technique requires that particles are chaotically moving in water, like photon correlation spectroscopy does, then it is important that the particles do not sediment. Particles in the above mentioned diameter range will not sediment even after several hours.

Furthermore, particles having a size below 50 nm typically contain very few target binding sites (the weight proportion of the target binding sites to the weight of the polymer is approximately in the range of from 1:1000 to 1:100 for low molecular weight template molecules) and are typically difficult to produce.

A MIP unit according to the present invention may also be in the form of a film having a thickness in the range of from 20 nm to 20 μm.

Such a film may be applied to (micro) electrodes in the form of e.g. interdigitated fingers. Upon target binding, a change in capacitance may be observed and detected.

It is well known that capacitance changes are related either to changes of the immobilized charges or to the changes of immobilized dipoles. In the present case target binding will result in a decrease of the number of charges and thus, the capacitance of the imprinted film will change.

A film in the above mentioned thickness range is suitable. When the thickness of the film is less than 20 nm, the film may be distorted by the polymer surface interaction, e.g. due to pinning of the polymer chains. In contrast, film thicknesses above 20 μm are impractical since the penetration of the target into the interior of the film is slower, and results in decreased occupation of target binding sites.

In alternative embodiments, the MIP unit further comprises an identity tag selected from the group comprising fluorophores, quantum dots and gold nanoparticles (not shown).

Such embodiments are suitable for use if the detection takes place in turbid samples; i.e. samples comprising lots of background signal particles.

In yet another aspect, the present invention relates to the use of a MIP unit according to the above for the detection of a target molecule in a solution.

This detection may be either qualitative or quantitative; i.e. the invention allows for both determining the presence of a target molecule of interest, but also the concentration of target molecules in a solution.

The present inventors have found that this may be achieved by measuring the rate of agglomeration of the above described MIP units in a solution.

The main physical and chemical parameters that govern the stability of colloidal solutions are well known (see, e.g. Robert J. Hunter, *Foundations of colloid Science*, vol. I, Clarendon Press, 1995, ISBN 0 19 855187 8) and will be described only briefly. Nano- or micro particles in colloidal solutions move chaotically due to the interaction with fluid molecules (so called Brownian motion). The Brownian motion results in collisions between the particles.

The intra particle encounter rate (the frequency of collisions) increases with increased particle concentration but decreases with increased particle size. The distance between the particles during such collisions decreases with decreased effective particle charge and with the increased ionic strength of the solution. The closer the particles approach each other during a collision, the higher is the probability that they will bind to each other.

During such collisions, if the particles bind to each other, they remain bound for some time after which they may fly apart again. If the time during which they are bound together is shorter then the time for next encounter the suspension will be stable. However if the time during which the two nanoparticles remain bound to each other is sufficiently long then next particle may collide with the small cluster, and bind to it. The cluster will therefore grow, i.e., particles in suspension will agglomerate, and the colloidal solution will become unstable.

Thus, the rate of agglomeration depends on how strong the particles bind to each other as well as on the encounter rate.

The present inventors have found that the binding strength and the encounter rate strongly depend on the charge of the target binding site of the MIP units as well as the charge of the template molecule.

When the target molecule and the MIPs are of opposite polarities, the adsorption is enhanced significantly and the MIP unit comprising bound target molecule will be neutralized. This allows for the essentially uncharged MIP particles to start agglomerate due to a higher probability of close intra particle associations.

The rate of agglomeration may also be manipulated by varying the pH of the solution for carrying out the agglomeration.

Figure 3:
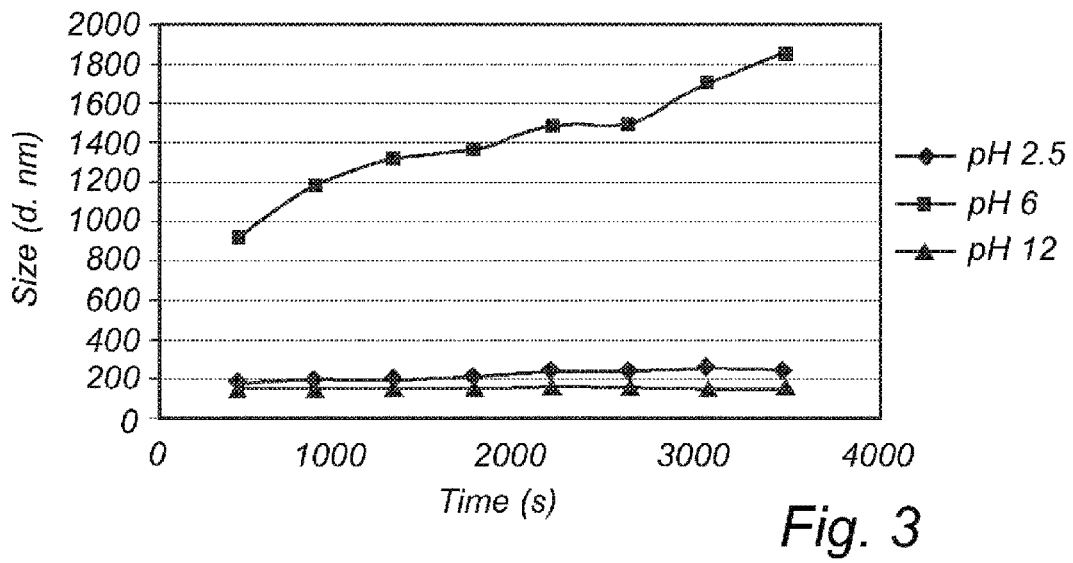
FIG. 3 illustrates the pH dependency on the rate of agglomeration.

As is illustrated in FIG. 3, the onset of agglomeration is pH-dependent. The pH may be chosen such that chargeable groups are generated within the target binding site(s) due to deprotonation or protonation of the functional monomer residues present in such site(s). Simultaneously, the template molecules should protonate or deprotonate at this pH such that the polarity of the template molecule is opposite that of the binding site.

In FIG. 3, propranolol is used as the template and the MIP unit; i.e. MIP particle is formed from methacrylic acid; i.e. the chargeable groups are represented by carboxyl groups. As the pKa of the carboxyl group is about 4 and the pKa of propranolol is about 9, both entities will be charged at a pH around 6; i.e. the carboxyl group will be deprotonated, and propranolol will be protonated. Accordingly, agglomeration occurs due to target molecule adsorption.

At sufficiently high pH (pH 12 in FIG. 3) the MAA is fully de-protonated and carries a negative charge. This makes the MIP particles repel each other to form stable colloidal solution. At the same time, at pH 12 propranolol exists as a neutral compound, therefore has low binding strength towards the negatively charged MIP particle binding sites. The overall effect is that particles do not aggregate regardless of if propranolol is present or absent in the sample.

At low pH (pH 2.5 in FIG. 3), the MIP particles are neutral because the carboxyl groups of the MAA are protonated leading to no net charge. The neutral particles do not bind propranolol even though the latter carries a net positive charge.

Accordingly, at pH 2.5 and pH 12, no electrostatic interaction between the target binding sites of the MIP particles and the target compound is present, and therefore no agglomeration occurs.

However, as may be observed at pH 6.0, the rate of agglomeration is significant as both the target binding sites of the MIP particles, and target compounds are charged. The adsorption of target compounds is enhanced and this is detected by agglomeration.

Hence, it is possible to tune the onset of agglomeration as a function of target uptake, and the induction of agglomeration may be achieved at a relatively minor target uptake. This allows to push the detection limit to lower target concentrations.

In a MIP unit according to the present invention, the effective charge state of the unit at a given pH will mainly determined by the number of target binding sites. This is due to the localization of surface-bound chargeable groups in the target binding sites, whereas the remaining particle surface (i.e. non-imprinted sites and non-specific imprinted sites) remains essentially uncharged.

Accordingly, upon binding with target molecules, the MIP units will have a net effective charge $Z_{eff}$ close to zero. This has an impact on the rate of agglomeration as the essentially uncharged MIP particles will start to cluster.

Hence, target molecule adsorption may be detected by simply measuring the net effective charge $Z_{eff}$ of the MIP unit(s). When $Z_{eff}$ decreases or increases (depending on the polarity of the charged groups), this may be an indication that a target molecule has been adsorbed. The net effective charge may e.g. be detected by monitoring the Z potential.

This detection scheme is suitable when the MIP unit is in the form of a film or a particle suspended in solution.

As the charge state of a target molecule and the MIP units may be determined, it is possible to choose a pH interval where both are charged in order to determine the rate of agglomeration or change of $Z_{eff}$.

Figure 4:
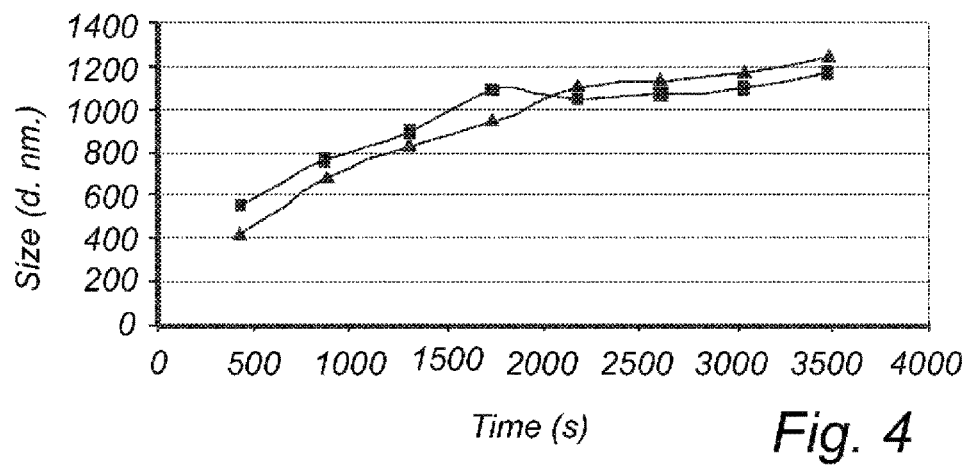
FIG. 4 illustrates the rate of agglomeration of MIP units of the invention as well as the effect of sonication after agglomeration.

The induction of agglomeration is further illustrated in FIG. 4. Here, MIP units; i.e. MIP particles in a concentration of 0.2 mg/ml have been exposed to R-propranolol at a concentration of 1.25 mM and the changes in size of the clustered MIP particles is significant.

When the particles reached a size of 1200 nm, they were subjected to sonication for about 45 minutes. After sonication, the experiment was repeated and the same agglomeration pattern was observed (illustrated by the triangular shaped curve in FIG. 4). This demonstrates that the MIP particles of the invention are reproducible and may be monitored in a controlled way.

Figure 5:
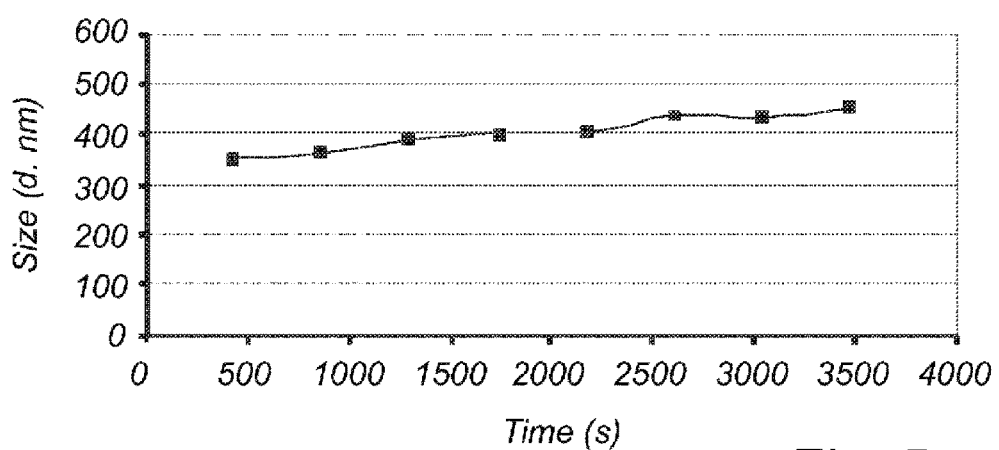
FIG. 5 illustrate the absence of agglomeration in the case of non-imprinted polymer (NIP) units.

In contrast, non-imprinted particles do not agglomerate substantially in contact with template molecules (FIG. 5).

The template molecules used during MIP unit production may be a chosen from the group comprising drug, hormone, enzyme, antibody, receptor, nucleic acid, virus, cell, tissue, pesticide and any other material including proteins.

Beta-blockers, especially propranolol and betaxolol are commonly used as template molecules during imprinting.

The present inventors have determined the rate of agglomeration at different concentrations of propranolol and betaxolol.

Figure 6A:
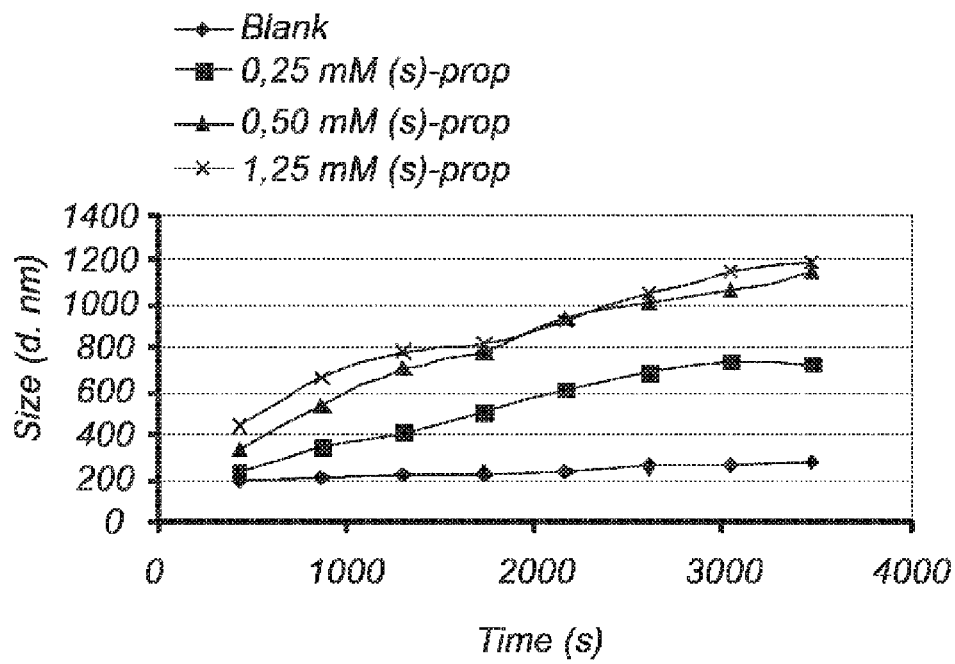
FIG. 6a illustrates the rate of agglomeration when propranolol in different concentrations is used as the target molecule.
Figure 6B:
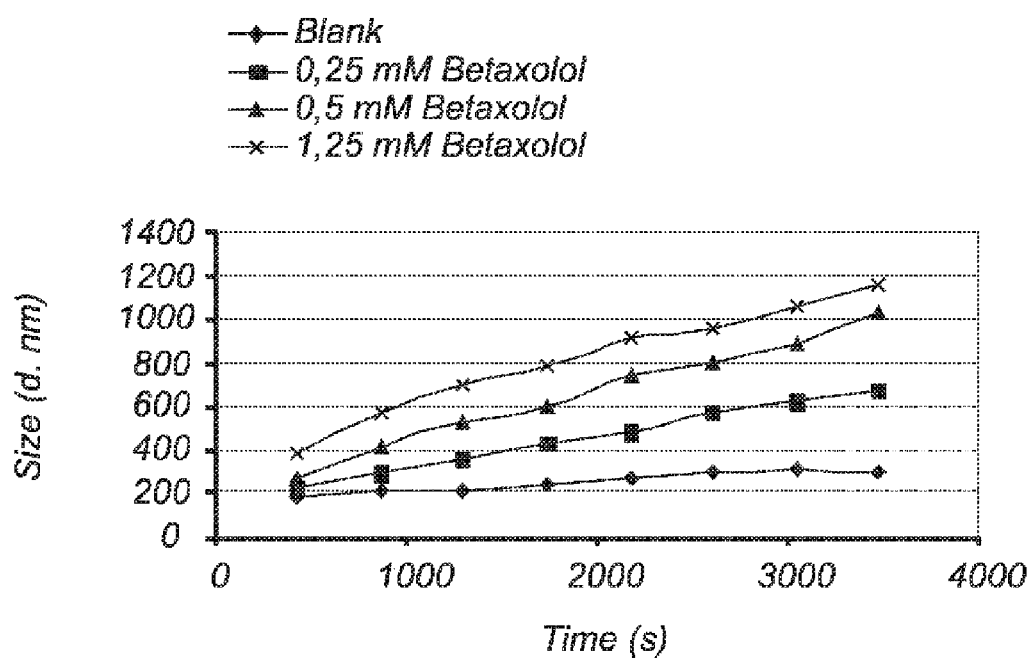
FIG. 6b illustrates the rate of agglomeration when betaxolol in different concentrations is used as the target molecule.

As is illustrated in FIGS. 6a and 6b, MIP units; i.e. MIP particles at a concentration of 0.02 mg/ml have been exposed to different concentrations of (s)-propranolol, and the rate of agglomeration increases significantly with higher propranolol and betaxolol concentrations.

The concentration of beta blocker, e.g. propranolol or betaxolol is typically in the range of from 0.05 to 2.5 mM.

MIP particles at a concentration of up to 0.2 mg/ml are suitable for use in the agglomeration assays.

MIP units of the present invention, may also be designed to evaluate the chirality of an imprinted polymer. This is not a trivial task which often requires sophisticated experimentation.

Figure 7:
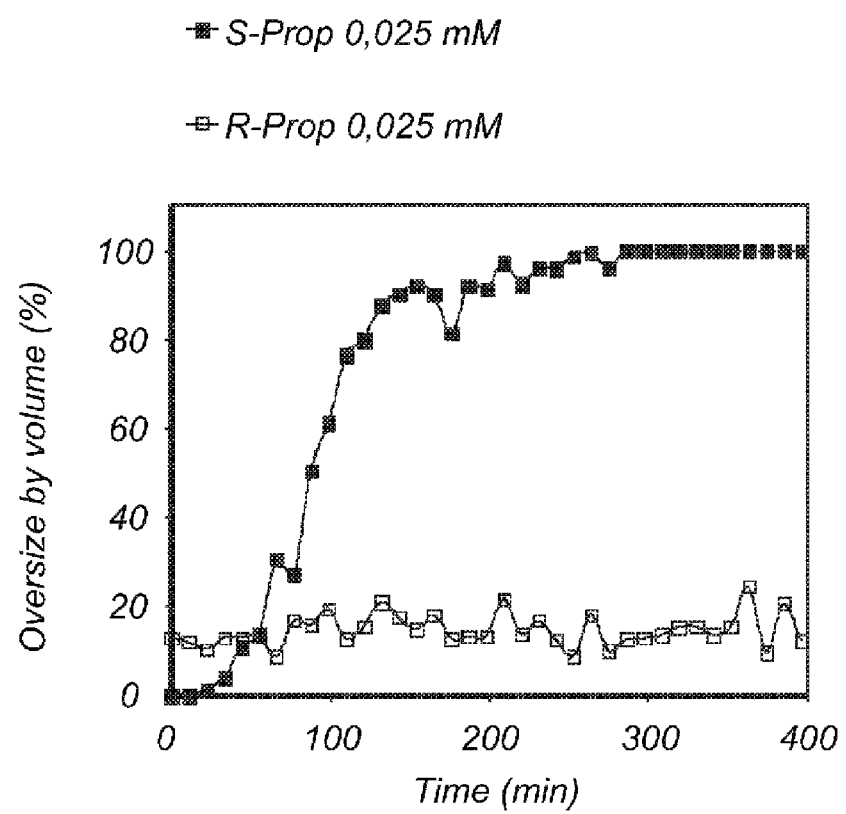
FIG. 7 shows the ability of the MIP units of the invention to distinguish between target molecules of different chirality.

Upon adsorption of a target molecule of proper chirality, MIP particles of the invention start to cluster, but targets of "wrong" chirality will not be absorbed, and hence no clustering will take place. This is illustrated in FIG. 7, where MIP units; i.e. MIP particles at a concentration of 0.02 mg/ml have been exposed to (s)-propranolol, and (r)-propranolol, respectively, and only (s)-propranolol is adsorbed by the MIP particles. This occurs even at low template molecule concentrations (0.025 mM in this specific example).

At high analyte concentrations this property disappears because there exists a plentitude of imprinted sites of "poorer quality" and these sites do not posses ability for chiral recognition.

The ability to distinguish chiral vs non-chiral sites by simply changing concentration of the analyte simplifies the imprint optimization. It also allows one to easily evaluate separation quality of pharmaceuticals where this property is of great importance.

The rate of agglomeration may be monitored by e.g. photon correlation spectroscopy (PCS) and static light scattering.

When the MIP units of the invention comprise an identity tag these may fluoresce and emit light, and as agglomerates grow, the emitted light intensity; i.e. agglomerated spots, becomes brighter. Such identity tags may also aid in distinguishing MIP particles amongst other particles in suspension, e.g. during Z potential measurements.

Z potential measurement may be suitable for detection of larger MIP particles, as well as when the MIP unit is in the form of a film.

It should be noted that MIP units of the invention, and the rate of agglomeration as means for measuring target adsorption, may be applied to many situations; i.e. it is by no means limited to the detection of waste-water contaminants.

The present inventors have also found a method for manufacturing customized MIP units having the above mentioned characteristics.

This method comprises:

(a) providing at least one MIP unit having a surface comprising at least one target binding site configured to resemble a target molecule and surface-bound chargeable groups (b) contacting the MIP unit(s) from step (a) with at least one template molecule in a first solvent allowing the template molecule(s) to bind to the MIP unit(s)

(c) passivating the surface-bound chargeable groups on the MIP unit(s) by adding a passivating agent (d) removing the template molecule(s) by washing in a second solvent.

The passivating agent binds to the surface of the unit(s) through bonds which remain stable upon washing in the second solvent.

As used herein the term "passivating" means eliminating surface-bound chargeable groups which may give rise to non-specific binding; i.e. converting undesired chargeable groups to uncharged groups which are hydrolytically stable.

Accordingly, a method according to the present invention allows for the preparation of MIP units which may be charged predominantly in the target binding sites right from the start.

The method of the invention is simple, inexpensive and allows for the mass production of customized MIP units having localized surface-bound chargeable groups within the target binding sites.

The first solvent typically has a pH which generates opposite polarities of the surface-bound chargeable groups, and the template molecule(s) respectively. Accordingly, the MIP unit will bind to the template molecule by means of electrostatic interaction.

A MIP unit having a surface comprising at least one target binding site configured to resemble a target molecule is typically provided by polymerizing functional monomers in the presence of a template and a cross-linking agent.

In embodiments of the invention, step (a) and step (b) may be performed simultaneously by polymerizing functional monomers in the presence of the template molecule(s) in the first solvent. In such cases, the MIP units are formed when functional monomers polymerize in a first solvent and in the presence of template molecules.

By way of example, the scheme below illustrates the generation of opposite polarities of the functional monomer methacrylic acid and the template molecule propranolol when these are mixed in a suitable solvent.

Scheme 1: Generation of surface charges of methacrylic acid (MAA) and propranolol

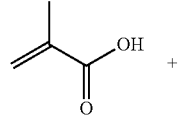

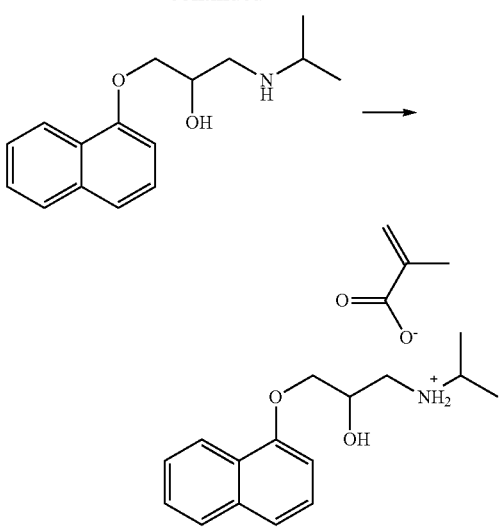

The MAA monomers are polymerized in the presence of propranolol in a first solvent. The first solvent has a pH which generates opposite polarities of the MAA monomers (negatively charged) and propranolol (positively charged).

By adjusting the pH to a pH which is larger than the $pK_a$ of the carboxyl group of MAA, most of the carboxyl groups in the polymer are de-protonated. In this case, the pH is 6.0 as the $pK_a$ of the carboxyl group is 4.0 In contrast, propranolol will carry a positive charge at this pH (pKa around 9).

For example, the solvent may comprise citric acid, acetate or phosphate buffer mixed with an organic component, e.g. acetonitrile or ethanol.

Since methacrylic acid is a hydrophobic monomer, an organic component is comprised in the solvent. The vol % of such organic components (e.g. acetonitrile or ethanol) may be varied between 25 to 75 vol %.

The first solvent is not limited to the above mentioned solvents, but may be adapted to the specific MIP and template used. In the present case when MAA and propranolol are used, the above mentioned combinations are suitable.

Upon polymerization in the presence of propranolol, a target binding site which is configured to resemble propranolol or its analogues is formed.

The scheme below illustrates the target binding site formed during polymerization:

Scheme 2: Surface-bound chargeable groups within the target binding site

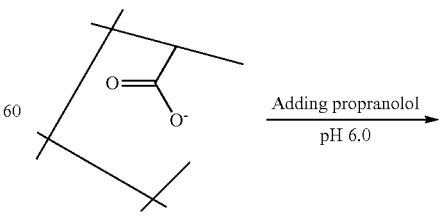

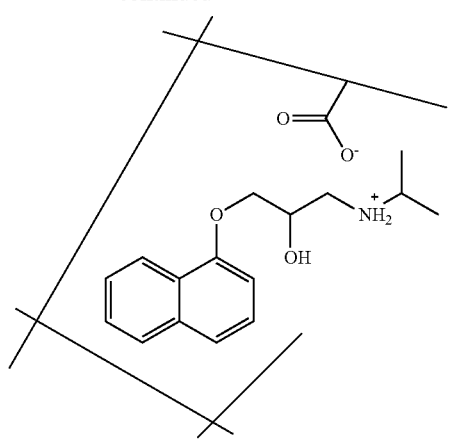

Surface bound chargeable groups within the MIP unit cavity; i.e. target binding site are formed from negatively charged carboxyl groups of the MAA residues.

When propranolol is added again, it will bind to the target binding cavity by means of (i) electrostatic interactions, (ii) complementarity in shape and size, and (iii) hydrophobic interactions between the $CH_3$ residues of propranolol and the MIP unit.

In alternative embodiments, 4-vinylpyridine is used as the monomer, and 4-vinylpyridine-2.4-dichlorophenoxyacetic acid (2,4-D) is used as the template.

In this case, the monomers are positively charged, and the templates are negatively charged in a neutral solvent.

Scheme 3: Generation of surface charges of 4-vinylpyridine and 4-vinylpyridine-2.4-dichlorophenoxyacetic acid (2,4-D)

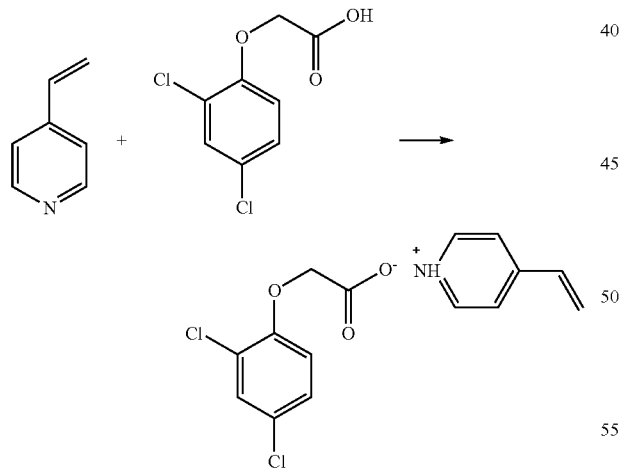

Upon polymerization in the presence of 2,4-D, a target binding site which is configured to resemble 2,4-D or its analogues is formed.

The scheme below illustrates the target binding site formed during polymerization:

Scheme 4: Surface-bound chargeable groups within the target binding site

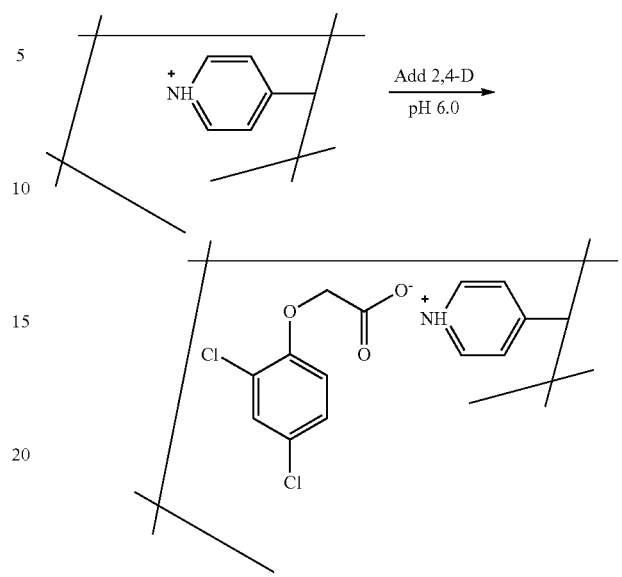

Surface bound chargeable groups within the MIP unit cavity are formed from the protonated pyridine group derived from the functional monomer 4-vinylpyridine.

As mentioned hereinbefore, template molecules may bind to the surface of a MIP unit both specifically (i.e. in the target binding sites) and non-specifically. The non-specific binding is undesired as it may generate false negative signals.

In order to remove non-specific binding at sites which are not configured to resemble a target of interest, as well as on non-imprinted sites on the MIP unit surface, a passivating agent is added which binds to the surface of the unit(s) through bonds which remain stable upon washing in a second solvent.

Such a second solvent; i.e. template elution solvent is known to a person skilled in the art.

In embodiments where the functional monomer contains an amino group, acetyl chloride can be used as the passivating agent.

The scheme below illustrates the passivation in an aprotic solvent; i.e. an organic solvent that does not exchange protons with a substance dissolved in it. Here, acetyl chloride is used as the passivating agent, and 2,4-D is used as the template molecule:

Scheme 5: Passivation of surface-bound chargeable groups of non-specific sites by treatment with acetyl chloride.

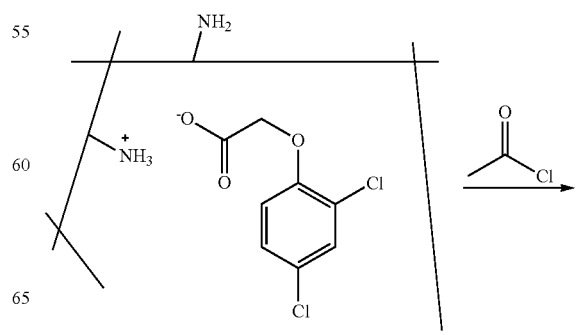

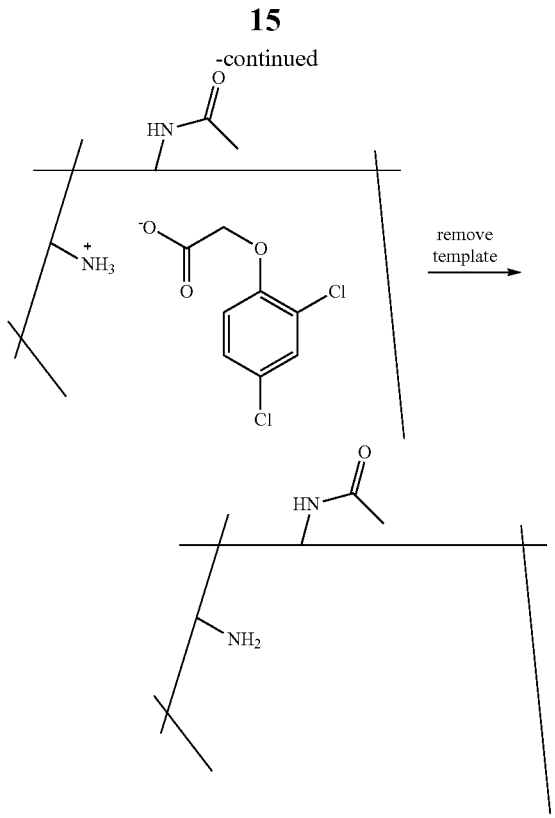

Here, the passivation occurs in a non-aqueous solvent. Under this condition only the template-occupied sites have charged amino group. The surface-bound chargeable amino group, because short of proton donor, is uncharged, and the formation of stable bonds through acylation takes place only for the uncharged amino group. After the passivation, the polymer can be used under aqueous condition where the pH can be adjusted with buffer to control the charge status of the free amino groups in the cavity.

When the passivating agent acetyl chloride is added to the MIP template molecule mixture, it reacts with the surface-bound chargeable amino groups and forms bonds, which are hydrolytically stable. In this example, the stable bonds formed result from acylation of the amino group; i.e. stable amide bonds are formed.

Since the template 2,4-D is specifically bound in the "correct" target binding site, the amino group located herein is protected from acylation and no passivation will take place at such site(s).

Upon removal of the template molecule, surface bound chargeable amino groups will remain in the target binding site, but the surface of the MIP unit will be essentially passivated; i.e. comprise substantially no surface-bound charges.

Accordingly, in embodiments of the invention, the surface-bound chargeable groups are represented by amino groups. In this case, acetyl chloride is a suitable passivating agent.

The choice of passivating agent depends on the structure of the functional monomer.

The passivating step of the above described method more particularly comprises:
removing template molecule(s) not specifically bound to the binding site(s) configured to resemble a target molecule such that surface-bound chargeable groups are exposed on the surface
forming stable bonds between the passivating agent and the surface-bound chargeable groups.

The passivating agent will compete with the template molecules non-specifically bound to the surface such that these are removed in contact with the passivating agent. However, template molecules bound in the correct target binding sites will not be removed as these remain bound due to complementarity in size and shape, electrostatic interaction and hydrophobic interactions within these cavities.

Upon addition of a passivating agent, surface-bound chargeable groups become exposed on the surface of the MIP unit.

The passivating agent is capable of forming stable bonds with such exposed surface-bound chargeable groups and these bonds remain hydrolytically stable even after template elution by washing with a second solvent.

The step of removing template molecule(s) not specifically bound to the binding site(s) configured to resemble a target molecule may be explained by the following relationship:

$$\exp\{-(H_{n/non\text{-}spec}-H_{non\text{-}spec})/kT\}:\exp\{-(H_{n/spec}-H_{spec})/kT\},$$

where T is the temperature and $H_{non\text{-}spec}$ is the enthalpy of the template bound to a non-specific site, $H_{spec}$ is the enthalpy of template specifically bound, while $H_{n/non\text{-}spec}$ and $H_{n/spec}$ are the enthalpies of the passivating agent that binds to the chargeable groups at non-specific or specific sites on the MIP unit, respectively.

The exchange equilibrium at non-specific sites occupied by template molecules will be $$\theta_n \sim 1/\{1+aKc_n\},$$

where a is a constant, K is the effective equilibrium reaction constant $\sim\exp\{-(H_{n/non\text{-}spec}-H_{non\text{-}spec})/kT$, $\theta_n$ is a fraction of sites occupied by the passivating agent and $c_n$ is the concentration of passivating agent in a solvent.

The factor in exponential is the enthalpy "gain" from "tearing-off" a target molecule and exchanging it for a passivating agent.

At room temperature the exponential may easily become very large and the coverage will than be close to 1. This is true especially when the non-specific target binding is electrostatic (typically ~10 kT). The specific binding is both electrostatic and hydrophobic (typically ~30 kT) while the passivating agent binding is stable; i.e. (semi) covalent, (typically ~200 kT). Thus, the removal of nonspecifically bound target molecule will be at least exp 3≈20 times more effective than the removal of specifically bound target.

In embodiments where methacrylic functional monomers and beta blockers are used as monomers, and template, respectively, diazomethane, phenyldiazomethane and acyl halide may be used as passivating agents.

Upon passivation, the surface-bound negatively chargeable carboxyl groups located in the non-specific sites are converted into non-charged ester groups by esterification reactions.

The bonds formed between the surface-bound chargeable groups and the passivating agent may e.g. be selected from ester bonds and amide bonds. However, other bonds which are hydrolytically stable also fall within the scope of the present invention.

In embodiments, the method further comprises the step of adding an identity tag selected from fluorophores, quantum dots and gold nanoparticles.

Typically, such identity tags are added during polymerization of functional monomers.

For example, amino or carboxyl groups of the functional monomers may be utilized to link the identity tags to the MIP units, thereby forming "bridges". Standard amino and carboxyl coupling reactions through DCC or EDC activation may also be used. Such coupling reactions are familiar for those skilled in the art While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

For example, the present invention is not limited to the use of specific functional monomers, template molecules etc., but any type of monomers and templates may be used. Neither is the invention limited to a specific application, but may be applied to any situation where target adsorption utilizing MIPs is appropriate.

EXAMPLES

Synthesis of Imprinted and Non-Imprinted Nanoparticles

Molecularly imprinted (MIP) nanoparticles were synthesized using a precipitation polymerization method described in a previous publication (Yoshimatsu et al., 2007). Briefly, the template molecule, (S)- or (R)-propranolol in its free base form (137 mg, 0.53 mmol) was dissolved in 40 ml of acetonitrile in a 150 mm×25 mm borosilicate glass tube equipped with a screw cap. MAA (113 mg, 1.31 mmol), TRIM (684 mg, 2.02 mmol) and AIBN (28 mg, 3 wt % of monomer) were then added. The solution was purged with a gentle flow of argon for 5 min and sealed under argon. Polymerization was carried out by inserting the borosilicate glass tube in a water bath pre-set at 60° C. for 24 h. After polymerization, particles were collected by centrifugation at 18000 rpm (38000 g) for 20 min. The template was removed by batch-mode solvent extraction with methanol containing 10% acetic acid (v/v), until no template could be detected from the washing solvent by spectrometric measurement (UV 290 nm). Polymer particles were finally washed with acetone and dried in a vacuum chamber. The resulting MIP particles, MIP(S) and MIP(R), were imprinted against (S)- or (R)-propranolol respectively. Non-imprinted reference polymers, NIP, were synthesized under identical conditions except for omission of the template.

Techniques Used for Measuring the Rate of Agglomeration
Dynamic Light Scattering—Photon Correlation Spectroscopy (PCS)

PCS may be used to determine the size distribution profile of MIP particles in a solution. When light hits the particles, the light scatters in all directions, and the fluctuations in scattering intensity may be measured.

These fluctuations arise because the number of particles within the measurement volume (the volume defined by the incident laser beam and the field of view of optical detector that is used to detect the scattered light) changes. The number of particles changes since MIP particles in solution are undergoing Brownian motion and enter into and move away from the measurement volume. Therefore, the intensity fluctuation carry information about the time scale of movement of the scatterers.

The so called normalized intensity autocorrelation function, which carries the information on the translational Brownian relaxation time, $\tau$, is measured. The relaxation time is a measure of how fast the particle moves (on average) and is closely related to a diffusion coefficient. The effective particle/agglomerate size is related to the relaxation time by:

$$\tau = (6\pi\eta/kTq^2) \times r,$$

where T and are solvent temperature and viscosity, respectively, while q is the light scattering vector, and is given by:

$$q = (4\pi n/\lambda_o) \times \sin(\theta/2)$$

with $\lambda_o$—wavelength of the incident light, n—MIP particle/agglomerate refractive index, and $\theta$—angle between the incident light and the detector. See R. Pecora, Dynamic light Scattering: Applications of Photon Correlation spectroscopy, Kluver Academic Publisher, 1985; for more information.

PCS is typically utilized when MIP particles are small, e.g. less than 500 nm.

Static Light Scattering

In order to detect the relative size of the agglomerated MIP particles, static light scattering may also be used. This technique uses the intensity traces at a number of angles to analyze scattering of particles in solution.

Changes in scattering intensity is measured at a few constant scattering angles. These are normalized to the intensity of the particle solution before target adsorption takes place.

A simple way to normalize the scattered intensities is by constructing the quotients of the type:

$$Q = \{I_{bsc}(0, \theta_{bsc}) - I_{bsc}(t, \theta_{bsc})\} / \{I_{fsc}(0, \theta_{fsc}) = I_{fsc}(t, \theta_{fsc})\}$$

for a few scattering angles, where $I_{bsc}(t, \theta_{bsc})$ is the back-scattered intensity at angle $\theta_{bsc}$ and time t (or time=0, respectively) while the $I_{fsc}(t, \theta_{fsc})$ is the forward scattered intensity at the angle $\theta_{fsc}$ and time t (or time=0, respectively). All the intensities are normalised to the forward transmitted intensity, $I_{tr}(t)$ (see FIG. 8) after the introduction of a target, which took place at time t=0.

When target adsorption leads to agglomeration the latter will be detected through the changes of Q.

The intensity of light scattered by small particles of diameters roughly from $0.1\lambda_o$-$100\lambda_o$ ($\lambda_o$ is the wavelength of the incident light) varies with the detection angle, particle size and the concentration of suspension.

Figure 8:
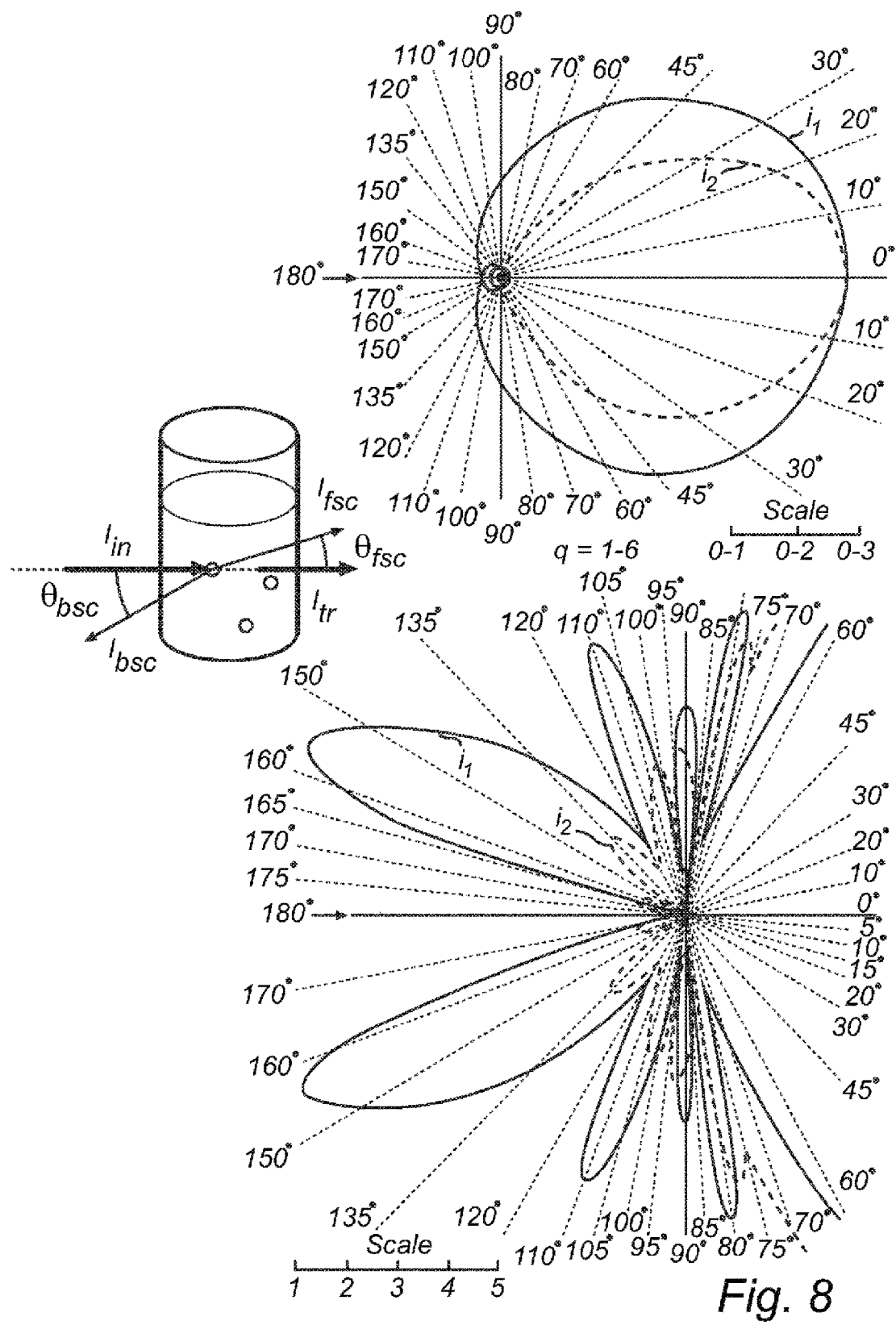
FIG. 8 illustrates the static light scattering approach of measuring the rate of agglomeration.

As shown in FIG. 8, the particles having diameter <600 nm scatter appreciable intensity in both the forward direction and backwards (except for certain directions, e.g., $\theta \approx 90°$. However the intensity of light scattered off particle clusters with diameters $>25\lambda_o$ shows pronounced minima in certain directions. The angular intensity scans can therefore be used to determine both the absolute sizes of particles and changes of their shapes upon agglomeration.

FIG. 8 shows also the geometry for the detection of agglutination via the static light scattering used here. The particles scatter the intensity of incident light, $I_{in}$, both in forward direction (intensity $I_{fsc}$) and backwards (intensity $I_{bsc}$).

At a given detection angle the scattered intensity depends strongly on the size of a particle and on the polarization of the incident beam, as is shown in the RHS of FIG. 8 {data after H. Blumer, Z. f. Physik, vol. 32 (1925) p. 199; see also Born and Wolf, Principles of Optics 5$^{th}$ ed., §13, Pergamon Press, Oxford 1975}. This property can be used to detect changes in particle sizes Target Binding as Measured by Agglomeration for MIP Particles of the Invention Compared to Non-Imprinted Polymer (NIP) Particles The rate of agglomeration using MIP particles of the invention was compared with that of non-imprinted polymer (NIP) particles (FIGS. 4 and 5).

MIP particles, and NIP particles, respectively in a concentration of 0.2 mg/ml, were added to a solution (pH 6.4) comprising template molecules (propranolol 1.25 mM).

As can be seen in FIG. 5, the rate of agglomeration was significant. When the particles reached a size of 1200 nm, the samples were sonicated for 45 minutes, and sonication, the analysis was repeated. The same agglomeration pattern was observed (triangular curve).

Non-imprinted polymer (NIP) units did not agglomerate significantly (FIG. 4).

The invention claimed is:

1. A method for detecting a target molecule in a solution that may comprise the target molecule, the method comprising:
   (a) providing molecularly imprinted polymer (MIP) units particles having a surface comprising at least one target binding site configured to resemble the target molecule and surface-bound chargeable groups in a first solvent comprising a buffer selected from the group consisting of citric acids, acetates and phosphates;
   wherein the MIP particles are produced by:
      (1) contacting MIP particles with at least one template molecule in the first solvent allowing said template molecule(s) to bind to said MIP particles;
      (2) passivating said surface-bound chargeable groups on said MIP particles by adding a passivating agent that binds to said surface of said particles through bonds which remain stable upon washing in a second solvent;
      (3) removing said template molecule(s) by washing in the second solvent, and
   (b) contacting said MIP units particles from step (a) with the solution;
   wherein pH of the first solvent is selected to be a pH which deprotonates the surface-bound chargeable groups and protonates the target molecule; or a pH which protonates the surface-bound chargeable groups and deprotonates the target molecule, such that polarity of the target molecule is opposite that of the surface-bound chargeable groups of the MIP units particles;
   wherein said detection is performed by measuring rate of agglomeration of said MIP units particles in said solution due to electrostatic interaction between target molecules and the at least one target binding site sites of the MIP units particles; and
   wherein an increased rate of agglomeration of said MIPS units indicates presence of the target molecule.

2. A method for detecting a target molecule in a solution that may comprise the target molecule, the method comprising:
   (a) providing molecularly imprinted polymer (MIP) units particles having a surface comprising at least one target binding site configured to resemble a target molecule and surface-bound chargeable groups in a first solvent comprising a buffer selected from the group consisting of citric acids, acetates and phosphates;
   wherein the MIP particles are produced by:
      (1) contacting MIP particles with at least one template molecule in the first solvent allowing said template molecule(s) to bind to said MIP particles;
      (2) passivating said surface-bound chargeable groups on said MIP particles by adding a passivating agent that binds to said surface of said particles through bonds which remain stable upon washing in a second solvent;
      (3) removing said template molecule(s) by washing in the second solvent, and
   (b) contacting said MIP units particles from step (a) with the solution; and
   wherein pH of the first solvent is selected to be a pH which deprotonates the surface-bound chargeable groups and protonates the target molecule; or a pH which protonates the surface-bound chargeable groups and deprotonates the target molecule, such that polarity of the target molecule is opposite that of the surface-bound chargeable groups of the MIP units particles;
   wherein said detection is performed by measuring net effective charge $Z_{eff}$ of said MIP units particles upon binding of target molecules to the at least one target binding site sites of the MIP units particles via electrostatic interaction; and
   wherein an increase or decrease in $Z_{eff}$ (depending on the polarity of the charged groups) indicates presence of the target molecule.

3. A method for detecting a target molecule in a solution that may comprise the target molecule, the method comprising:
   (a) providing molecularly imprinted polymer (MIP) units particles having a surface comprising at least one target binding site configured to resemble the target molecule and surface-bound chargeable groups in a solvent comprising a buffer selected from the group consisting of citric acids, acetates and phosphates; and
   (b) contacting said MIP units particles from step (a) with the solution; and
   wherein pH of the solvent is selected to be a pH which deprotonates the surface-bound chargeable groups and protonates the target molecule; or a pH which protonates the surface-bound chargeable groups and deprotonates the target molecule, such that polarity of the target molecule is opposite that of the surface-bound chargeable groups of the MIP units particles;
   wherein said detection is performed by measuring rate of agglomeration of said MIP units particles in said solution due to electrostatic interaction between target molecules and the at least one target binding site sites of the MIP units particle;
   wherein an increased rate of agglomeration of said MIPS units indicates presence of the target molecule; and
   wherein at least 80% of a total amount of surface-bound chargeable groups are located in the at least one target binding site enabling electrostatic interaction with the target molecule to occur in the at least one target binding site.

4. A method for detecting a target molecule in a solution that may comprise the target molecule, the method comprising:
   (a) providing molecularly imprinted polymer (MIP) units particles having a surface comprising at least one target binding site configured to resemble the target molecule and surface-bound chargeable groups in a solvent comprising a buffer selected from the group consisting of citric acids, acetates and phosphates; and
   (b) contacting said MIP units particles from step (a) with the solution; and
   wherein pH of the solvent is selected to be a pH which deprotonates the surface-bound chargeable groups and protonates the target molecule; or a pH which protonates the surface-bound chargeable groups and deprotonates the target molecule, such that polarity of the target molecule is opposite that of the surface-bound chargeable groups of the MIP units particles;

wherein said detection is performed by measuring net effective charge $Z_{eff}$ of said MIP units particles upon binding of target molecules to the at least one target binding site sites of the MIP units particles via electrostatic interaction;

wherein an increase or decrease in $Z_{eff}$ depending on the polarity of the charged groups) indicates presence of the target molecule; and wherein at least 80% of a total amount of surface-bound chargeable groups are located in the at least one target binding site enabling electrostatic interaction with the target molecule to occur in the at least one target binding site.

5. A method for detecting a target molecule in a solution that may comprise at least one of the target molecule, the method comprising:

(a) providing at least one molecularly imprinted polymer unit (MIP) particle having a surface comprising at least one target binding site and at least one surface-bound chargeable group in a solvent comprising a buffer selected from the group consisting of citric acids, acetates and phosphates; and (b) contacting said at least one molecularly imprinted polymer unit particle from step (a) with said solution; and wherein pH of the solvent is selected to be a pH which deprotonates the at least one surface-bound chargeable group and protonates the at least one target molecule; or a pH which protonates the at least one surface-bound chargeable group and deprotonates the at least one target molecule, such that polarity of the at least one target molecule is opposite that of the at least one surface-bound chargeable group groups of the at least one MIP units particle;

wherein said detection is performed by measuring rate of agglomeration of said at least one molecularly imprinted polymer unit particle in said solution due to electrostatic interaction between the at least one target molecule and the at least one target binding site of the at least one molecularly imprinted polymer unit particle; and wherein an increased rate of agglomeration of said MIPS units indicates presence of the target molecule.

6. A method for detecting a target molecule in a solution that may comprise at least one of the target molecule, the method comprising:

(a) providing at least one molecularly imprinted polymer unit (MIP) particle having a surface comprising at least one target binding site and at least one surface-bound chargeable group in a solvent comprising a buffer selected from the group consisting of citric acids, acetates and phosphates; and (b) contacting said at least one molecularly imprinted polymer unit particle from step (a) with said solution; and wherein pH of the solvent is selected to be a pH which deprotonates the at least one surface-bound chargeable group and protonates the at least one target molecule; or a pH which protonates the at least one surface-bound chargeable group and deprotonates the at least one target molecule, such that polarity of the at least one target molecule is opposite that of the surface-bound chargeable groups of the at least one MIP units particle;

wherein said detection is performed by measuring net effective charge $Z_{eff}$ of said at least one molecularly imprinted polymer unit particle upon binding of the at least one target molecule to the at least one target binding site of the at least one molecularly imprinted polymer unit particle via electrostatic interaction; and wherein an increase or decrease in $Z_{eff}$ (depending on the polarity of the charged groups) indicates presence of the target molecule.

7. The method of claim 1, wherein the MIP particles have a particle size between 50 nm to 5 μm.

8. The method of claim 2, wherein the MIP particles have a particle size between 50 nm to 5 μm.

9. The method of claim 3, wherein the MIP particles have a particle size between 50 nm to 5 μm.

10. The method of claim 4, wherein the MIP particles have a particle size between 50 nm to 5 μm.

11. The method of claim 5, wherein the at least one MIP particle has a particle size between 50 nm to 5 μm.

12. The method of claim 6, wherein the at least one MIP particle has a particle size between 50 nm to 5 μm.

* * * * *